United States Patent
Ida et al.

(10) Patent No.: US 8,238,633 B2
(45) Date of Patent: Aug. 7, 2012

(54) IMAGE PROCESSING APPARATUS, RADIOGRAPHIC IMAGE SYSTEM, AND IMAGE PROCESSING METHOD AND PROGRAM

(75) Inventors: Noriaki Ida, Kanagawa (JP); Hirofumi Sawada, Kanagawa (JP); Akiko Kanagawa, Kanagawa (JP); Daiki Harada, Kanagawa (JP); Satomi Yamada, Kanagawa (JP); Minoru Takami, Kanagawa (JP); Yasunori Ohta, Kanagawa (JP); Naoki Mochizuki, Kanagawa (JP); Ryo Ono, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/241,010

(22) Filed: Sep. 22, 2011

(65) Prior Publication Data

US 2012/0076273 A1 Mar. 29, 2012

(30) Foreign Application Priority Data

Sep. 29, 2010 (JP) ................................. 2010-219693

(51) Int. Cl.
 *G06K 9/00* (2006.01)
 *G01N 23/05* (2006.01)
(52) U.S. Cl. .................... 382/128; 250/390.02
(58) Field of Classification Search .................. 382/128, 382/129, 130, 131, 132, 133, 134; 378/4, 378/8, 21–27; 600/407, 410, 411, 425, 427; 250/390.02; 128/915, 916, 920, 922
See application file for complete search history.

(56) References Cited

U.S. PATENT DOCUMENTS

| 6,061,465 | A  | * | 5/2000 | Nakajima ..................... 382/132 |
| 6,243,485 | B1 |   | 6/2001 | Murakami |
| 6,356,651 | B2 | * | 3/2002 | Murakami ..................... 382/128 |
| 2002/0039084 | A1 | * | 4/2002 | Yamaguchi ..................... 345/1.1 |
| 2004/0151358 | A1 | * | 8/2004 | Yanagita et al. .............. 382/132 |
| 2009/0220174 | A1 |   | 9/2009 | Saito |

FOREIGN PATENT DOCUMENTS

| JP | 10-071138 A | 3/1998 |
| JP | 10-143634 A | 5/1998 |
| JP | 10-162156 A | 6/1998 |
| JP | 10-248830 A | 9/1998 |
| JP | 10-275213 A | 10/1998 |
| JP | 2002-368975 A | 12/2002 |
| JP | 2009-201872 A | 9/2009 |

* cited by examiner

*Primary Examiner* — Abolfazl Tabatabai
(74) *Attorney, Agent, or Firm* — McGinn IP Law Group, PLLC

(57) ABSTRACT

An image processing apparatus capable of clipping a diagnostic region while retaining the pixel information of the original radiographic image even when the subject is imaged aslant. The image processing apparatus applies trimming processing to a radiographic image acquired by an imaging apparatus for acquiring a radiographic image of a subject and includes an image rotation unit for rotating the radiographic image so that the subject is aligned with a given direction to produce a display image, a diagnostic region designation unit for designating a first diagnostic region clipped with a diagnostic region designation frame represented by a rectangle for the display image, and a trimming processing unit for calculating a second diagnostic region in the radiographic image from a rotation amount of the display image and diagnostic region information representing the first diagnostic region and applying trimming processing to the radiographic image to clip the second diagnostic region.

16 Claims, 3 Drawing Sheets

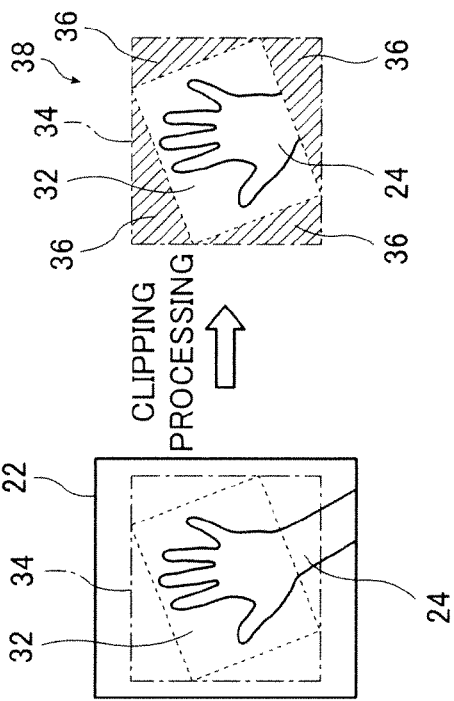

IMAGE PROCESSING APPARATUS, RADIOGRAPHIC IMAGE SYSTEM, AND IMAGE PROCESSING METHOD AND PROGRAM

BACKGROUND OF THE INVENTION

The present invention relates to an image processing apparatus, a radiographic image system, and an image processing method and program for applying trimming processing to a radiographic image acquired by an imaging apparatus for acquiring a radiographic image of a subject.

Radiographic images acquired by irradiating a subject, which may be, for example, a patient, with X ray or other radiation are widely used by doctors as diagnostic images. Presently, the wide use of CR (computer-aided radiography) type or DR (digital radiography) type radiographic imaging apparatus has led to practical applications of radiographic image systems for medical use for digitally processing, for example, acquisition, image processing, and display of radiographic images.

A radiographic image system is equipped with, for example, an imaging apparatus for acquiring a radiographic image of a subject and outputting the digital image data thereof, an image processing apparatus for applying image processing to the acquired radiographic image, and an image diagnosis apparatus for displaying the image-processed radiographic image. These imaging apparatus, image processing apparatus, and image diagnosis apparatus, for example, are installed, for example, in different places in a hospital and connected to each other via network.

The image data of the radiographic image of the subject acquired by the imaging apparatus is outputted from the imaging apparatus and inputted via network to the image processing apparatus for image processing. Subsequently, in a diagnosis given by a doctor, the image data after image processing is outputted from the image processing apparatus, inputted via network to the image diagnosis apparatus, and displayed on the image diagnosis apparatus. The doctor gives diagnosis by referring to the diagnostic image displayed on the image diagnosis apparatus.

When the subject is imaged aslant, there arises a need of the image processing apparatus performing, for example, image rotation processing or trimming frame rotation processing (or trimming processing wherein a region is freely designated) in order to clip only an appropriate diagnostic region.

JP 2009-201872 A describes a chest image rotation apparatus comprising a chest image entering means for entering a chest image, a centrum region extraction means for extracting a centrum region from the entered chest image, a centrum direction calculation means for calculating the centrum direction in the chest image based on the extracted centrum region, a chest image rotation means for rotating the chest image so that the calculated centrum direction is perpendicular to the horizontal sides of the chest image, and an output means for outputting the rotated chest image.

JP 2002-368975 A describes an image processing apparatus that performs image data conversion so that the image rotates in an image trimming processing in an image processing apparatus for processing image data containing an image of at least a part of a human body.

SUMMARY OF THE INVENTION

When the subject is imaged aslant and hence the radiographic image needs to be rotated, the subject that is imaged aslant may indeed be made upright, making the trimming easier to perform. However, the radiographic image rotation may necessitate production of pixel information by complementation processing when there is no pixel information as a result of the radiographic image rotation processing. As a result, there arises a problem that an image that is different from the original radiographic image is recorded.

Further, in the trimming frame rotation processing (or trimming frame deformation processing), a diagonal line is drawn on the inclined subject, so that unlike in a common application with a rectangular region substantially parallel to the left and right sides and the upper and lower sides of the display screen direction or the display region, the operation is complicated, which poses a problem at a site where medical images are acquired and therefore efficient handling is required.

An object of the present invention is to provide an image processing apparatus, a radiographic image system, and an image processing method and program capable of readily clipping a diagnostic region while retaining the pixel information of the original radiographic image even when the subject is imaged aslant by producing a display image from the radiographic image and designating a trimming frame for the display image.

In order to attain the object described above, the present invention provides an image processing apparatus for applying trimming processing to a radiographic image acquired by an imaging apparatus for acquiring the radiographic image of a subject, the image processing apparatus comprising:

an image rotation unit for rotating the radiographic image so that the subject is aligned with a given direction to produce a display image, a diagnostic region designation unit for designating a first diagnostic region to be clipped with a diagnostic region designation frame represented by a rectangle for the display image, and a trimming processing unit for calculating a second diagnostic region in the radiographic image from a rotation amount of the display image and diagnostic region information representing the first diagnostic region and applying the trimming processing to the radiographic image so as to clip the second diagnostic region.

Also, the present invention provides a radiographic image system comprising:

an imaging apparatus for acquiring a radiographic image and outputting image data of an imaged area of the radiographic image, the image processing apparatus described in claim 1, and an image diagnosis apparatus for receiving image data of a diagnostic image outputted from the image processing apparatus and displaying a diagnostic image corresponding to the received image data.

Also, the present invention provides an image processing method of applying trimming processing to a radiographic image acquired by an imaging apparatus for acquiring the radiographic image of a subject, the image processing method comprising:

an image rotating step of rotating the radiographic image so that the subject is aligned with a given direction to produce a display image, a diagnostic region designating step of designating a first diagnostic region to be clipped with a diagnostic region designation frame represented by a rectangle for the display image, and a trimming processing step of calculating a second diagnostic region in the radiographic image from a rotation amount of the display image and diagnostic region information representing the first diagnostic region and applying the trimming processing to the radiographic image so as to clip the second diagnostic region.

Also, the present invention provides a non-transitory computer readable recording medium having therein stored a program for causing a computer to execute the steps in the image processing method described above.

As described above, even when the subject is imaged aslant, a diagnostic region can be readily clipped while retaining the pixel information of the original radiographic image. Further, data volume can be reduced in data compression by encompassing a diagnostic region in a rectangle having left and right sides and upper and lower sides that are substantially parallel to the left and right sides and the upper and lower sides of the original radiographic image, respectively, and masking the portions excluding the diagnostic region in the rectangle.

BRIEF DESCRIPTION OF THE DRAWINGS

FIGS. 3A to 3D are explanatory views illustrating an example of rotation, trimming, and clipping processing.

DETAILED DESCRIPTION OF THE INVENTION

The image processing apparatus of the invention and the radiographic image system using the image processing apparatus will be described in detail below based upon preferred embodiments illustrated in the attached drawings.

Figure 1:
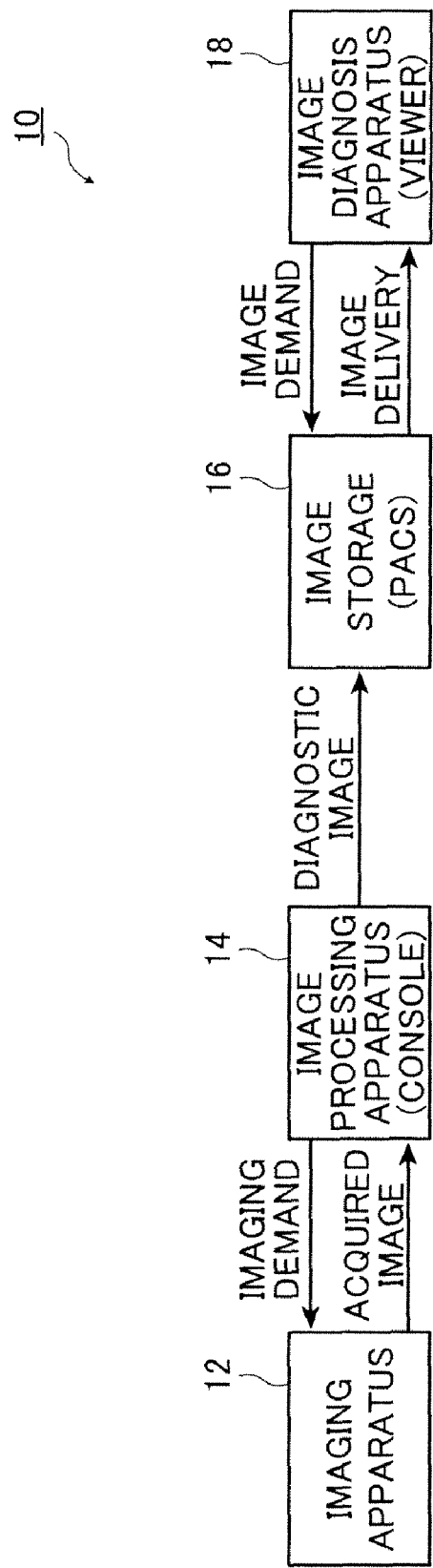
FIG. 1 is a block diagram illustrating the image processing apparatus of the invention.

FIG. 1 is a block diagram of an embodiment representing a configuration of a radiographic image system according to the invention.

A radiographic image system 10 illustrated in FIG. 1 comprises an imaging apparatus 12, an image processing apparatus (console) 14, an image storage (PACS) 16, and an image diagnosis apparatus (viewer) 18. These components are installed, for example, in different places in a hospital and connected to each other via network. Image data and demands (demand signals) of various kinds are transmitted and received via network.

The imaging apparatus 12 irradiates a subject with X ray or other radiation according to an imaging demand entered from the image processing apparatus 14 demanding acquisition of a radiographic image to acquire a radiographic image of the subject and outputs digital image date of the acquired radiographic image. The image data of the radiographic image outputted from the imaging apparatus 12 is inputted to the image processing apparatus 14. The imaging apparatus 12 may be of any type including, for example, a CR type and a DR type imaging apparatus.

A CR type imaging apparatus stores the radiation having passed through the subject in an imaging plate (IP), scans the IP with a laser beam, reads the photo-stimulated luminescence fluorescent light then emitted from the IP, and obtains image data through computer processing.

A DR type imaging apparatus detects the radiation having passed through the subject with a solid state radiation detector such as a flat panel detector (FPD) to obtain digital image data of a radiographic image. Examples of a DR type imaging apparatus include a fixed type having the FPD incorporated in a standing-position imaging table or a lying-position imaging table and a transportable type having the FPD housed in a cassette and attached to the imaging apparatus when imaging is performed.

Subsequently, the image processing apparatus (console) 14 transmits the imaging demand for acquiring a radiographic image to the imaging apparatus 12 as described above and receives image data of the radiographic image (original image) of the subject for which the imaging demand has been made from the imaging apparatus 12.

The image processing apparatus 14 comprises a radiation field region extraction means, a subject region extraction means, a rotation processing means, and a trimming processing means. The image processing apparatus 14 applies radiation field recognition processing, trimming processing, and other processing to the original image and outputs diagnostic image data obtained by extracting only a region of interest (an image region necessary for a doctor to give diagnosis). The diagnostic image data is inputted to the image storage 16.

The radiation field region extraction means performs radiation field recognition processing for automatically extracting image data of an image of an irradiated region (irradiated radiation field region) among the image data of the original image. The present applicant has already proposed various processing methods of radiation field recognition processing in, for example, JP 10-071138 A, JP 10-143634 A, JP 10-162156 A, JP 10-275213 A, and JP 10-248830. The present invention may use various radiation field recognition processing methods including those described in these publications. Therefore, detailed descriptions thereof are omitted here.

The subject region extraction means extracts a subject region from the radiation field region image and detects the vertical or horizontal direction of the subject.

In the rotation processing, the rotation processing means rotates the radiation field region image based on the vertical or horizontal direction of the subject so that the subject and the diagnostic region designation frame are substantially parallel or substantially perpendicular. The rotation processing means outputs the radiation field region image having undergone the rotation processing as display image and outputs the rotation amount of the radiation field region image.

The trimming processing means designates a first diagnostic region for the display image with a diagnostic region designation frame represented by a rectangle entered by an imaging technician produces diagnostic region information representing the first diagnostic region. When the imaging technician gives a trimming completion instruction, the trimming processing means calculates a second diagnostic region corresponding to the first diagnostic region in the radiation field region image from the display image rotation amount and diagnostic region information representing the first diagnostic region.

The diagnostic region information representing the first diagnostic region is information representing a rectangle and is represented by the coordinates of at least one vertex and the lengths of sides intersecting with each other at right angles of the first diagnostic region or represented by the coordinates representing two vertexes located at opposite angles in the first diagnostic region.

Then, the trimming processing means clips the smallest rectangle (trimming frame) containing the second diagnostic region from the radiation field region image and outputs the rectangle as diagnostic image. The second diagnostic region is a region tilted with respect to the radiation field region image by a rotation amount for the above-described display image; the left and right sides and the upper and lower sides of the trimming frame are parallel to the left and right sides and the upper and lower sides of the radiation field region image, respectively. Thus, the vertexes of the second diagnostic region are in contact with the sides of the trimming frame. The portions of the trimming frame excluding the second diagnostic region are subjected to masking processing for reduction of image data.

Subsequently, the image storage (PACS) 16 is an image data base for storing the image data of all the diagnostic images and imaging conditions entered from the image processing apparatus 14. In response to the delivery demand entered from the image diagnosis apparatus 18 requesting delivery of a diagnostic image, the image storage 16 delivers (outputs) image data of a diagnostic image of a subject designated by the image diagnosis apparatus 18 from among the image data of all the stored diagnostic images.

The image diagnosis apparatus (viewer) 18 outputs a diagnostic image delivery demand to the image storage 16 as described above and receives image data of the diagnostic image of the subject for which delivery has been demanded from the image storage 16 and displays a diagnostic image corresponding to the image data.

Figure 2:
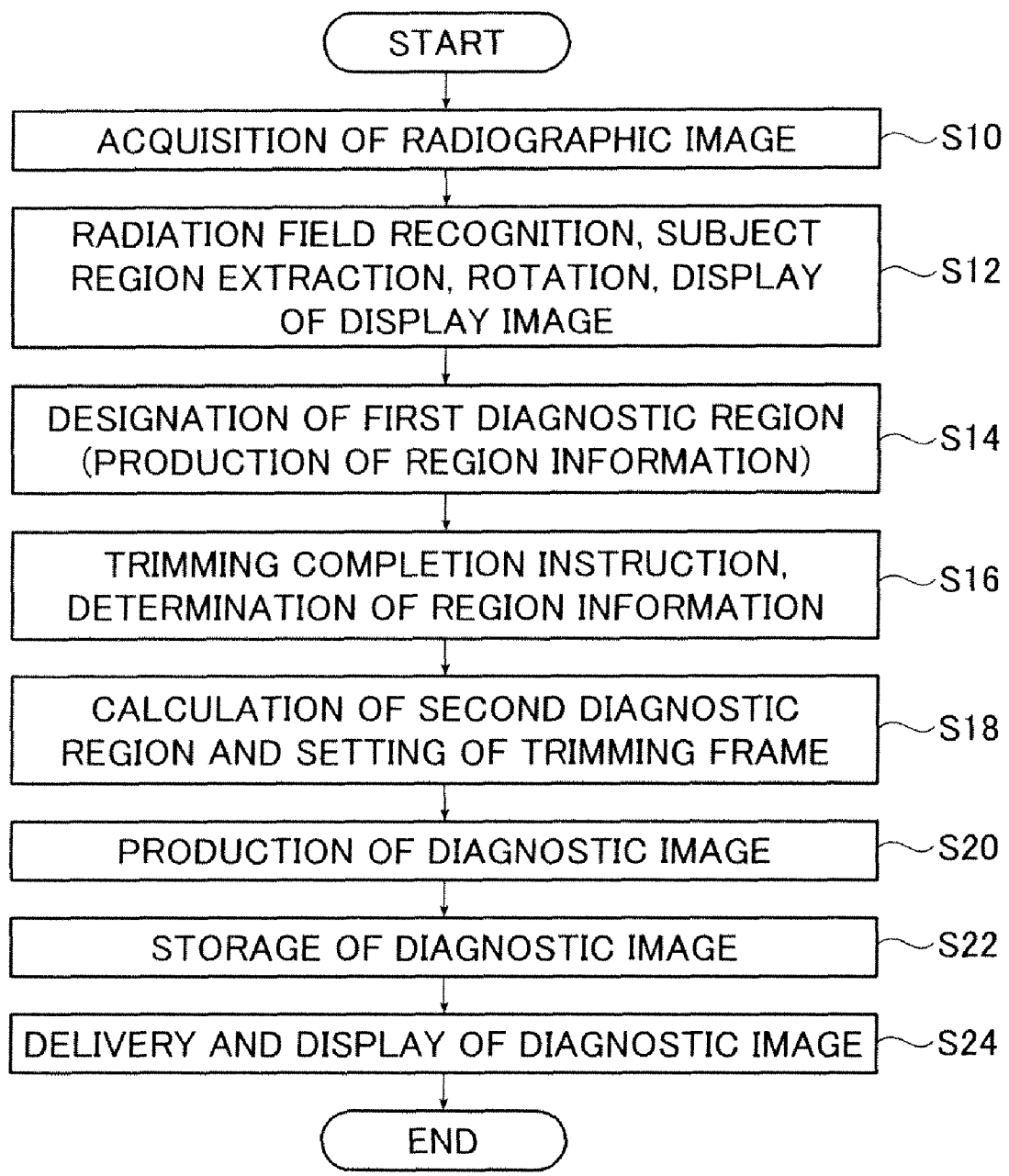
FIG. 2 is a flowchart illustrating an example of a processing flow from imaging to trimming processing.

Next, the operation of the radiographic image system 10 will be described referring to the flow chart illustrated in FIG. 2 and to FIG. 3.

During acquisition of a radiographic image, the imaging technician inputs a radiographic acquisition instruction via an input means by, for example, depression of an imaging button to the image processing apparatus 14. Thus, the radiographic image acquisition demand is outputted from the image processing apparatus 14 and inputted to the imaging apparatus 12, where the subject undergoes radiography (step S10). Upon completion of imaging, the image data of the acquired radiographic image is outputted from the imaging apparatus 12 and inputted to the image processing apparatus 14.

In the image processing apparatus 14, first the image data (original data) for the imaged area of the radiographic image undergoes radiation field recognition processing to produce a radiation field region image 22 as illustrated in FIG. 3A. The subject region extraction means extracts a subject region from the radiation field region image and detects the vertical or horizontal direction of a subject 24.

The rotation processing means applies rotation processing to the radiation field region image 22 based on the detected vertical or horizontal direction of the subject 24 so that the subject 24 and a diagnostic region designation frame 28 (e.g., a frame entered with a mouse) are substantially parallel to each other. The rotated radiation field region image is displayed as display image 26 as illustrated in FIG. 3B and displayed on a monitor, not shown, provided in the image processing apparatus 14 (step S12). The subject 24 and the diagnostic region designation frame 28 need not necessarily be substantially parallel and may form any angle, that is, the rotation processing may be performed with any rotation amount.

Then, the imaging technician enters a first diagnostic region 30, which is designated by the diagnostic region designation frame 28, via input means into the image processing apparatus 14 referring to the display image 26 displayed on the monitor, and the trimming processing means produces diagnostic region information representing the first diagnostic region 30. Upon completion of entry of the first diagnostic region 30, the imaging technician enters a trimming completion instruction (completion of entry of the first diagnostic region) to determine the diagnostic region information representing the first diagnostic region 30 (step S16). The display image 26 is discarded after the diagnostic region information representing the first diagnostic region 30 is determined but may be stored.

When the diagnostic region information representing the first diagnostic region 30 is determined, a second diagnostic region 32 corresponding to the first diagnostic region 30 is calculated in the radiation field region image 22 from the rotation amount of the display image 26 and the diagnostic region information representing the first diagnostic region 30 as illustrated in FIG. 3C. In brief, the first diagnostic region 30 is established in the radiation field region image 22. Therefore, the second diagnostic region 32 does not require the complementation processing and has the same pixel information as the original radiographic image. Further, there is set in the radiation field region image 22 a trimming frame 34, which is the smallest rectangle that contains the second diagnostic region 32 (step S18).

As illustrated in FIG. 3D, the trimming frame 34 is clipped from the radiation field region image 22 and generated and outputted as diagnostic image 38 (image data of the diagnostic image) (step S20). Portions 36 of the trimming frame 34 excluding the second diagnostic region 32 are unnecessary portions and preferably subjected to masking processing for reduction in volume of image data. To extract only the second diagnostic region 32 and contain it in a still smaller film size, the rotation processing may be newly performed or the rotation amount for the display image 26 may be used to perform rotation equal to that applied to the display image 26 to output the area excluding the masked portions (i.e., the second diagnostic region 32). In this case, the original pixel information is not retained.

Upon completion of the image processing by the image processing apparatus 14, the image processing apparatus 14 outputs the image data of the diagnostic image. The image data of the diagnostic image is inputted to the image storage 16 for storage.

After the diagnostic image is stored in the image storage 16 (step S22), the image diagnosis apparatus 18 outputs a diagnostic image delivery demand to the image storage 16, which, in response to the delivery demand, retrieves and outputs image data of a diagnostic image of a subject designated by the image diagnosis apparatus 18 from among the image data of all the stored diagnostic images (step S24).

Upon receiving the image data of the diagnostic image of the subject for which the delivery demand has been made, the image diagnosis apparatus 18 displays the diagnostic image corresponding to the image data (step S24).

A doctor or an interpreter of the diagnostic image gives diagnosis referring to the diagnostic image displayed on the image diagnosis apparatus 18.

As described above, even when the subject is imaged aslant, the radiographic image system 10 can readily clip a diagnostic region while retaining the pixel information of the original radiographic image. Further, data volume can be reduced in data compression by encompassing a diagnostic region in a rectangle having left and right sides and upper and lower sides that are substantially parallel to the left and right sides and the upper and lower sides of the original radiographic image, respectively, and masking the portions excluding the diagnostic region in the rectangle.

According to the invention, the steps taken in the above image processing method may be formed into a radiographic imaging program for causing a computer to execute such steps or as an image processing program for causing a computer to function as individual means for implementing the steps in the image processing method, or for causing a computer to function as individual means for constituting the above image processing apparatus.

Further, the above image processing program of the present invention may be configured as a computer-readable medium or as a computer-readable memory.

While the image processing apparatus and the image processing method and program of the present invention have been described in detail, the above embodiments are only illustrative and various changes and modifications may be made without departing from the spirit and scope of the invention.

We claim:

1. An image processing apparatus for applying trimming processing to a radiographic image acquired by an imaging apparatus for acquiring the radiographic image of a subject, the image processing apparatus comprising:
   an image rotation unit for rotating the radiographic image so that the subject is aligned with a given direction to produce a display image;
   a diagnostic region designation unit for designating a first diagnostic region to be clipped with a diagnostic region designation frame represented by a rectangle for the display image; and
   a trimming processing unit for calculating a second diagnostic region in the radiographic image from a rotation amount of the display image and diagnostic region information representing the first diagnostic region and applying the trimming processing to the radiographic image to clip the second diagnostic region.

2. The image processing apparatus according to claim 1, wherein the trimming processing comprises clipping a smallest rectangle having left and right sides and upper and lower sides of a trimming frame represented by a rectangle that are parallel to left and right sides and upper and lower sides of the radiographic image, respectively, and encompassing the second diagnostic region.

3. The image processing apparatus according to claim 2, wherein the trimming processing further comprises masking processing for masking portions of the smallest rectangle excluding the second diagnostic region.

4. The image processing apparatus according to claim 1, wherein the diagnostic region information comprises lengths of sides that intersect coordinates of at least one vertex of the first diagnostic region at right angles or coordinates of two vertexes located at opposite angles of the first diagnostic region.

5. A radiographic image system, comprising:
   an imaging apparatus for acquiring a radiographic image and outputting image data of an imaged area of the radiographic image;
   the image processing apparatus described in claim 1; and
   an image diagnosis apparatus for receiving image data of a diagnostic image outputted from the image processing apparatus and displaying a diagnostic image corresponding to the received image data.

6. The image processing apparatus according to claim 1, wherein the second diagnostic region comprises a region corresponding to the first diagnostic region in the radiographic image.

7. The image processing apparatus according to claim 1, wherein the trimming processing comprises clipping a trimming frame represented by a rectangle that includes sides parallel to corresponding sides of the radiographic image, and encompassing the second diagnostic region.

8. The image processing apparatus according to claim 1, wherein the second diagnostic region includes a same pixel information as pixel information of the radiographic image of the subject.

9. The image processing apparatus according to claim 1, wherein the trimming processing comprises clipping a trimming frame represented by a rectangle.

10. The image processing apparatus according to claim 9, wherein vertexes of the second diagnostic region contact sides of the trimming frame.

11. An image processing method of applying trimming processing to a radiographic image acquired by an imaging apparatus for acquiring the radiographic image of a subject, the image processing method comprising:
    an image rotating of the radiographic image so that the subject is aligned with a given direction to produce a display image;
    a diagnostic region designating of a first diagnostic region to be clipped with a diagnostic region designation frame represented by a rectangle for the display image; and
    a trimming processing for calculating a second diagnostic region in the radiographic image from a rotation amount of the display image and diagnostic region information representing the first diagnostic region and applying the trimming processing to the radiographic image to clip the second diagnostic region.

12. A non-transitory computer readable recording medium having therein stored a program for causing a computer to execute the image processing method described in claim 11.

13. The image processing method according to claim 11, wherein the trimming processing comprises clipping a smallest rectangle having left and right sides and upper and lower sides of a trimming frame represented by a rectangle that are parallel to left and right sides and upper and lower sides of the radiographic image, respectively, and encompassing the second diagnostic region.

14. The image processing method according to claim 13, wherein the trimming processing further comprises masking processing for masking portions of the smallest rectangle excluding the second diagnostic region.

15. The image processing method according to claim 11, wherein the diagnostic region information comprises lengths of sides that intersect coordinates of at least one vertex of the first diagnostic region at right angles or coordinates of two vertexes located at opposite angles of the first diagnostic region.

16. The image processing method according to claim 11, wherein the second diagnostic region comprises a region corresponding to the first diagnostic region in the radiographic image.

* * * * *